United States Patent
Williams et al.

(10) Patent No.: US 10,773,087 B1
(45) Date of Patent: *Sep. 15, 2020

(54) LEAD DELIVERY FOR HIS-BUNDLE PACING

(71) Applicants: Terrell M. Williams, Brooklyn Park, MN (US); Pugazhendhi Vijayaraman, Mountain Top, PA (US)

(72) Inventors: Terrell M. Williams, Brooklyn Park, MN (US); Pugazhendhi Vijayaraman, Mountain Top, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/897,574

(22) Filed: Jun. 10, 2020

Related U.S. Application Data

(63) Continuation of application No. 15/267,195, filed on Sep. 16, 2016.

(51) Int. Cl.
| | |
|---|---|
| *A61N 1/372* | (2006.01) |
| *A61N 1/375* | (2006.01) |
| *A61M 25/00* | (2006.01) |
| *A61N 1/05* | (2006.01) |
| *A61M 25/06* | (2006.01) |

(52) U.S. Cl.
CPC ......... *A61N 1/372* (2013.01); *A61M 25/0041* (2013.01); *A61M 25/0662* (2013.01); *A61N 1/0573* (2013.01); *A61N 1/37518* (2017.08); *A61M 25/0068* (2013.01); *A61M 2210/125* (2013.01); *A61N 2001/0585* (2013.01)

(58) Field of Classification Search
CPC .. A61N 1/372; A61N 1/0573; A61N 1/37518; A61M 25/0662
See application file for complete search history.

(56) References Cited

U.S. PATENT DOCUMENTS

| | | |
|---|---|---|
| 5,246,014 A | 9/1993 | Williams et al. |
| 5,306,263 A | 4/1994 | Voda |
| 5,617,854 A | 4/1997 | Munsif |
| 5,772,693 A | 6/1998 | Brownlee |
| 5,851,226 A | 12/1998 | Skubitz et al. |
| 5,876,385 A | 3/1999 | Ikari et al. |
| 5,987,746 A | 11/1999 | Williams |
| 6,004,280 A | 12/1999 | Buck et al. |

(Continued)

OTHER PUBLICATIONS

Kawashima et al., A macroscopic anatomical investigation of atrioventricular bundle locational variation relative to the membranous part of the ventricular septum in elderly human hearts, Surgical & Radiologic Anatomy, Feb. 19, 2005, pp. 206-213, vol. 27, Springer-Verlag, Heidelberg, Germany.

(Continued)

*Primary Examiner* — Richard G Louis
(74) *Attorney, Agent, or Firm* — Lund IP, PLLC

(57) ABSTRACT

A guiding catheter and method of its use are presented wherein the catheter includes an elongate catheter shaft having a proximal region and a distal region and a length. The shaft defines a distal region and includes a distal tip. The distal region defines an arc of approximately 180 degrees and having a radius of 0.3 inches to 0.6 inches. The distal tip forms a half turn of a left-hand helix having a pitch of 0 inches to 0.4 inches. The unique shape of the distal region allows the distal tip be perpendicularly aligned with the septal wall of the right atrium at the His bundle location when the catheter is advanced therein.

21 Claims, 6 Drawing Sheets

(56) References Cited

U.S. PATENT DOCUMENTS

| | | | |
|---|---|---|---|
| 6,066,126 | A | 5/2000 | Li et al. |
| 6,214,016 | B1 | 4/2001 | Williams et al. |
| 6,408,214 | B1 | 6/2002 | Williams et al. |
| 6,937,897 | B2 | 8/2005 | Min et al. |
| 7,056,294 | B2 | 6/2006 | Khairkhahan et al. |
| 7,082,335 | B2 | 7/2006 | Klein et al. |
| 7,177,704 | B2 | 2/2007 | Laske et al. |
| 7,647,124 | B2 | 1/2010 | Williams |
| 7,657,325 | B2 | 2/2010 | Williams |
| 7,729,782 | B2 | 6/2010 | Williams et al. |
| 8,100,883 | B1 | 1/2012 | Johnson |
| 8,332,042 | B2 | 12/2012 | Williams |
| 8,606,369 | B2 | 12/2013 | Williams et al. |
| 9,504,801 | B2 | 11/2016 | Dangoisse |
| 9,579,501 | B2 | 2/2017 | Shuros et al. |
| 2003/0130713 | A1 | 7/2003 | Stewart et al. |
| 2007/0203555 | A1* | 8/2007 | Williaims ......... A61M 25/0041 607/122 |
| 2009/0105724 | A1 | 4/2009 | Yoshizaki et al. |
| 2013/0338641 | A1* | 12/2013 | Worley ............. A61M 25/0041 604/528 |
| 2018/0078772 | A1 | 3/2018 | Williams et al. |

OTHER PUBLICATIONS

Medtronic, C315 Catheter: For the SelectSecure® Pacing lead system, Dec. 2008, Medtronic, Inc., Minneapolis, Minnesota.

* cited by examiner

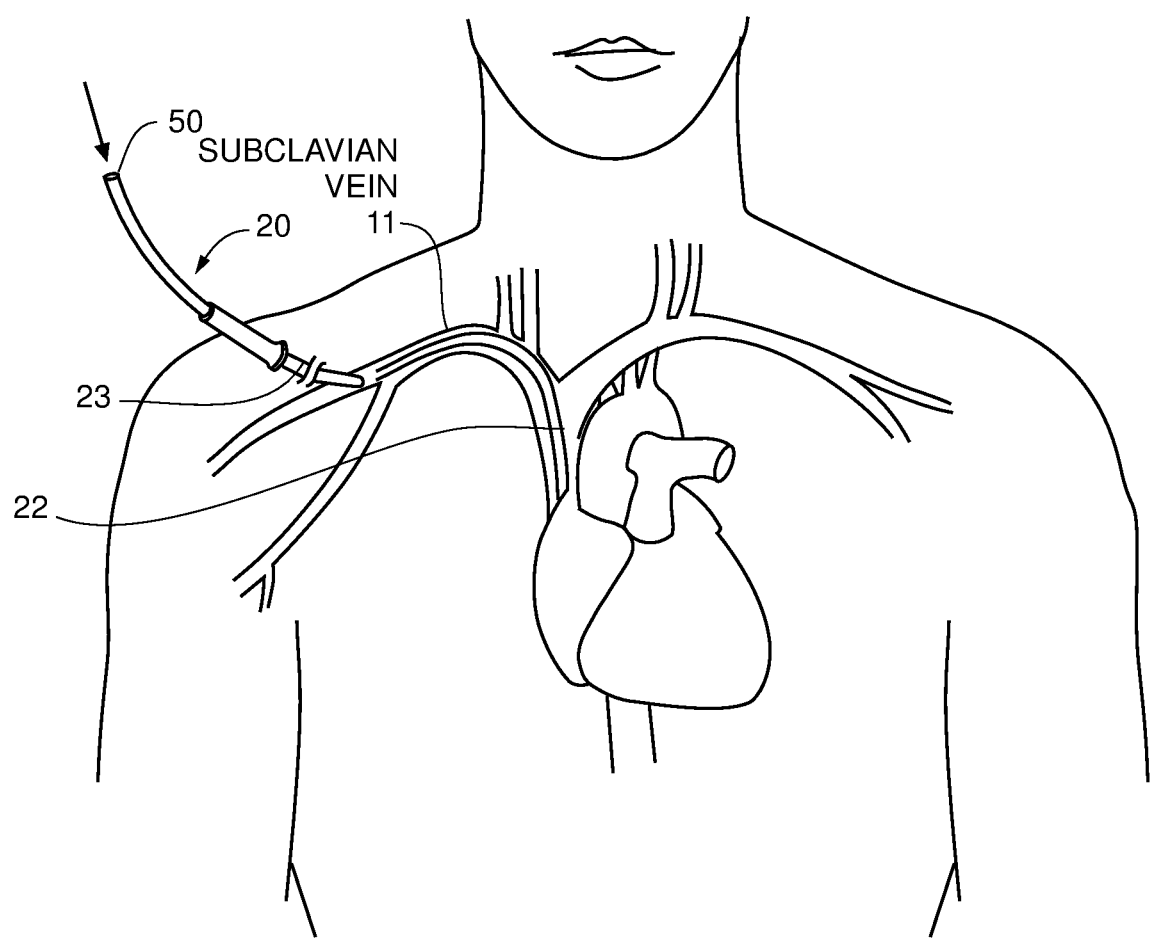

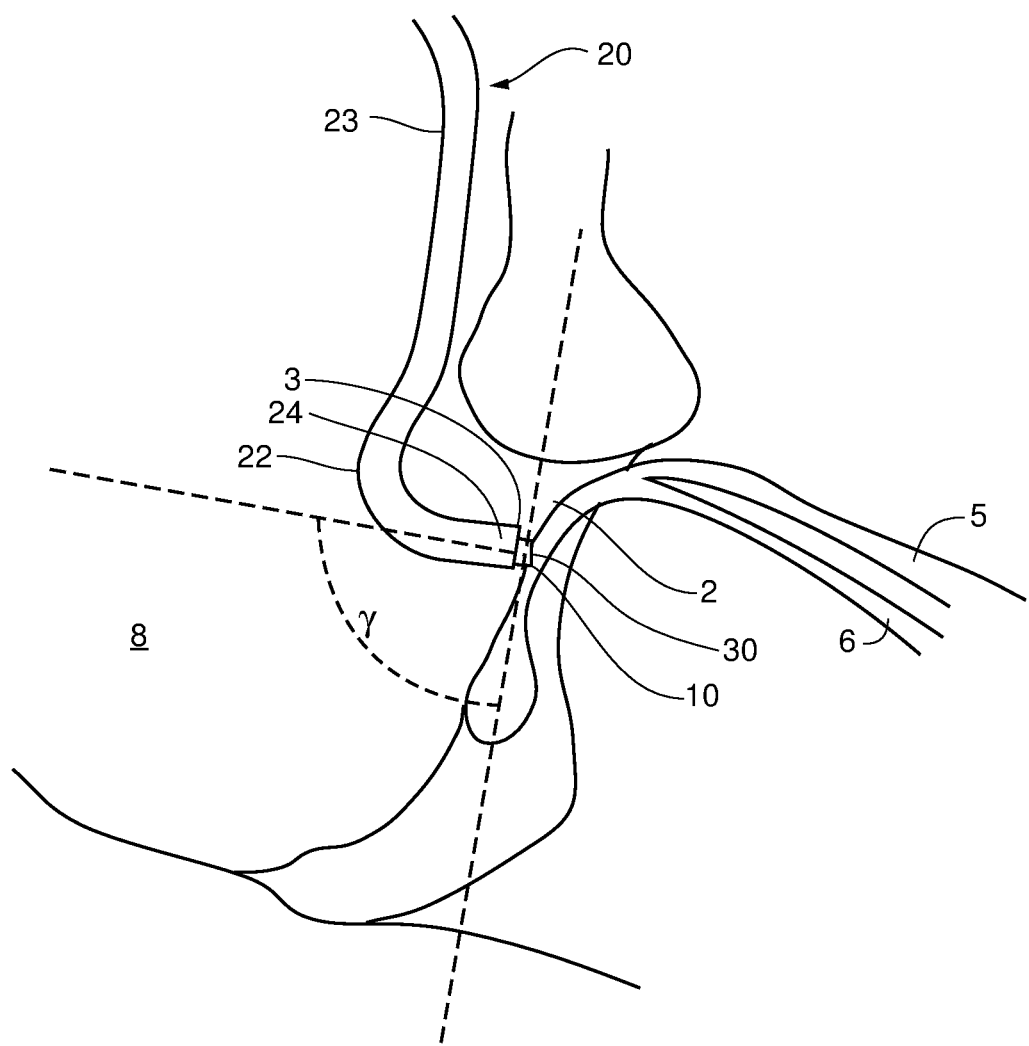

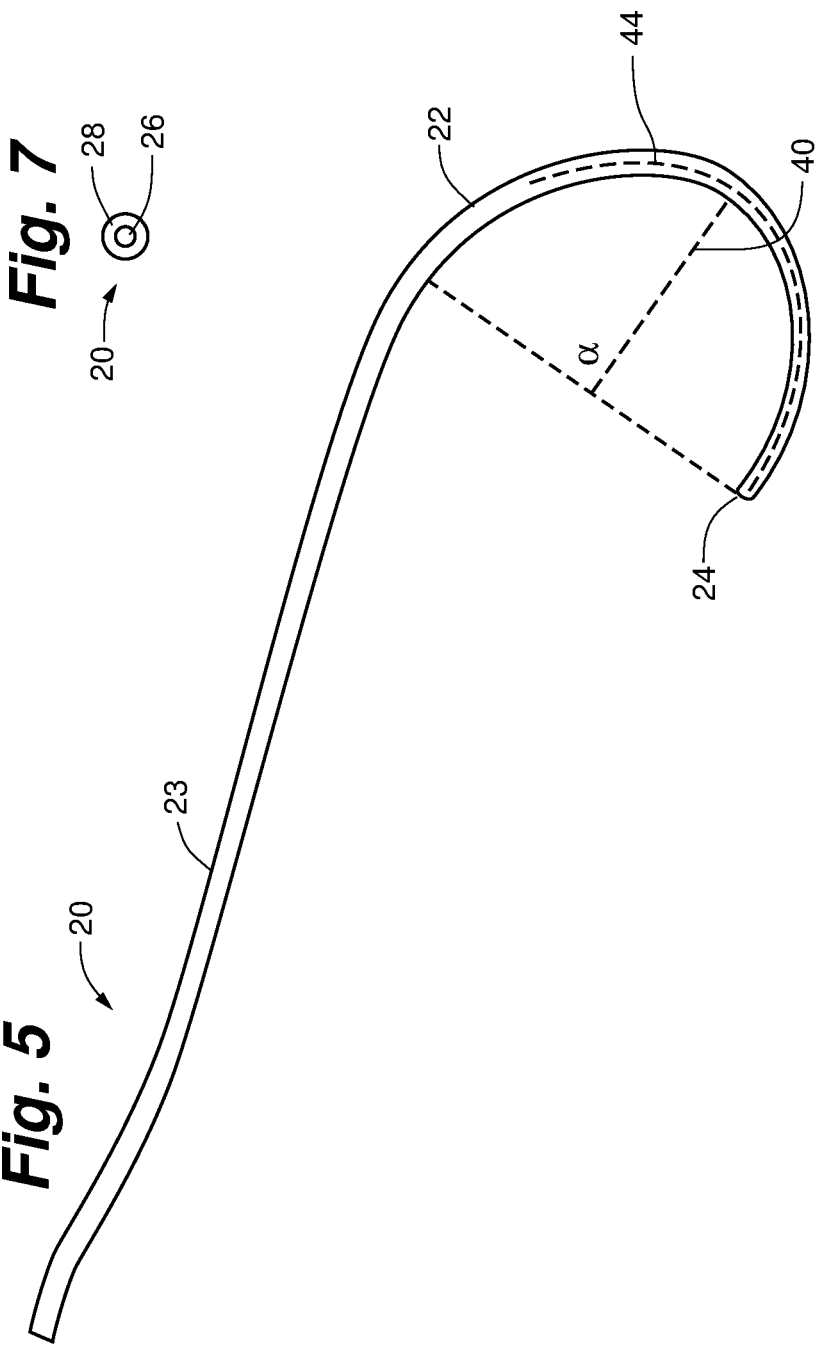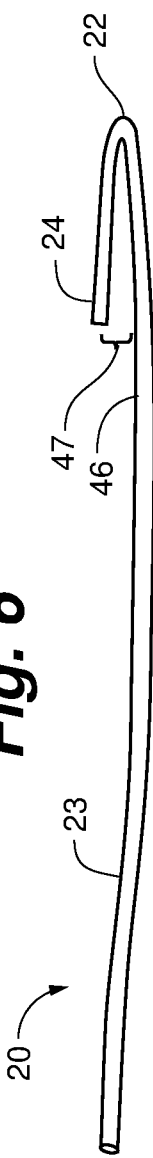

US 10,773,087 B1

LEAD DELIVERY FOR HIS-BUNDLE PACING

RELATED APPLICATION

This application claims priority to U.S. patent application Ser. No. 15/267,195, filed Sep. 16, 2016, which is incorporated by reference herein.

FIELD OF THE INVENTION

Embodiments of this disclosure relate to catheters and treatment methods using such catheters to deliver a pacing lead to the bundle of His by way of right side access to the heart through the right subclavian vein.

BACKGROUND

Guiding catheters are well known devices used to locate and cannulate vessels for a variety of medical procedures. They are of particular use in cardiac access procedures such as those involved in the implantation of cardiac pacing leads. Cardiac pacing leads are flexible, and historically, stylets have been inserted into the lumen of hollow leads to stiffen and allow the lead to be bent to aid in lead placement. Stylets are still in common use but are inadequate to provide precise control to reach and place a lead at the small target His bundle. Typically, when right side approach is desired it involves accessing the heart via the left subclavian vein, the cephalic vein and more rarely the internal or external jugular vein, or femoral vein. For catheter lead placement, a guide wire is advanced into the heat from the access site. The guiding catheter is then advanced through the vasculature and into the heart over the guidewire; once in position the guidewire is removed. A pacing lead is then advanced through the guiding catheter to be deployed at various regions in the heart.

Typically, pacing leads are deployed to various locations in the heart depending on the nature of the heart condition necessitating the pacing procedure. Conventional ventricular pacing typically involves implanting a lead at the apex of the right ventricle. This placement is still often utilized today even in the face of published evidence of the deleterious effects of bypassing the His/Purkinje system, otherwise known as the cardiac conduction system.

Pacemaker lead electrodes have been placed in or on the heart in a position that bypasses the His/Purkinje system since the inception of pacing in 1957. Directly stimulating the myocardium is and has been the standard of care even though His bundle pacing has been known and tried occasionally. It is believed that His bundle pacing is not widely practiced because it presents a small target and is very hard to reach successfully. This increases "fluro time" which is a detriment to both patient and physician. Another factor is that there is no wide recognition of the value of His pacing. At present there is a paucity of catheters that can facilitate His bundle pacing. When, for various reasons, the pacemaker must be implanted on the patient's right side and right subclavian vein used to reach the heart the target is still the myocardium and not the His bundle. It should be noted for completeness that the His bundle is accessed on the atrial aspect of the annulus of the tricuspid valve, just above the attachment of the septal valve leaflet.

The present disclosure describes embodiments of a catheter and method for its use in delivering a pacing lead to the His bundle at the septal wall. The cardiac conduction system is comprised in part of His bundle which resides between the atrioventricular (AV) node, and the bifurcation of left bundle branch (LBB) and right bundle branch (RBB). This anatomic location is regarded as a difficult target to reach. Embodiments of the present invention have overcome this difficulty.

SUMMARY

Embodiments of the present disclosure are directed to a unique guiding catheter configuration which allows for the precise delivery of pacing leads to the septal wall of the right atrium, above the anterior tricuspid valve septal leaflet, in proximity to the His bundle and from a right side approach to the heart. The catheter interacts with the anatomy to allow both precise and quick access to the His bundle as it presents in the right heart.

BRIEF DESCRIPTION OF THE DRAWINGS

FIG. 3 is an anatomical illustration of a patient and the manner in which the embodiment shown in FIG. 2 initially accesses the vasculature prior to advancement into the heart.

FIG. 4 is a detailed view of the distal region and tip of the catheter shown in FIGS. 2 and 3 at the target site.

FIG. 5 is a perspective view of the catheter embodiment shown in FIGS. 2-4 in its preformed or default shape prior to insertion into a patient.

FIG. 6 is a side view of the catheter embodiment shown in FIG. 5 illustrating the angle of the distal tip relative to the plane defined by the proximal region of the catheter.

FIG. 7 is a cross-sectional view of the catheter embodiment shown in FIGS. 5-6.

DETAILED DESCRIPTION

Figure 1:
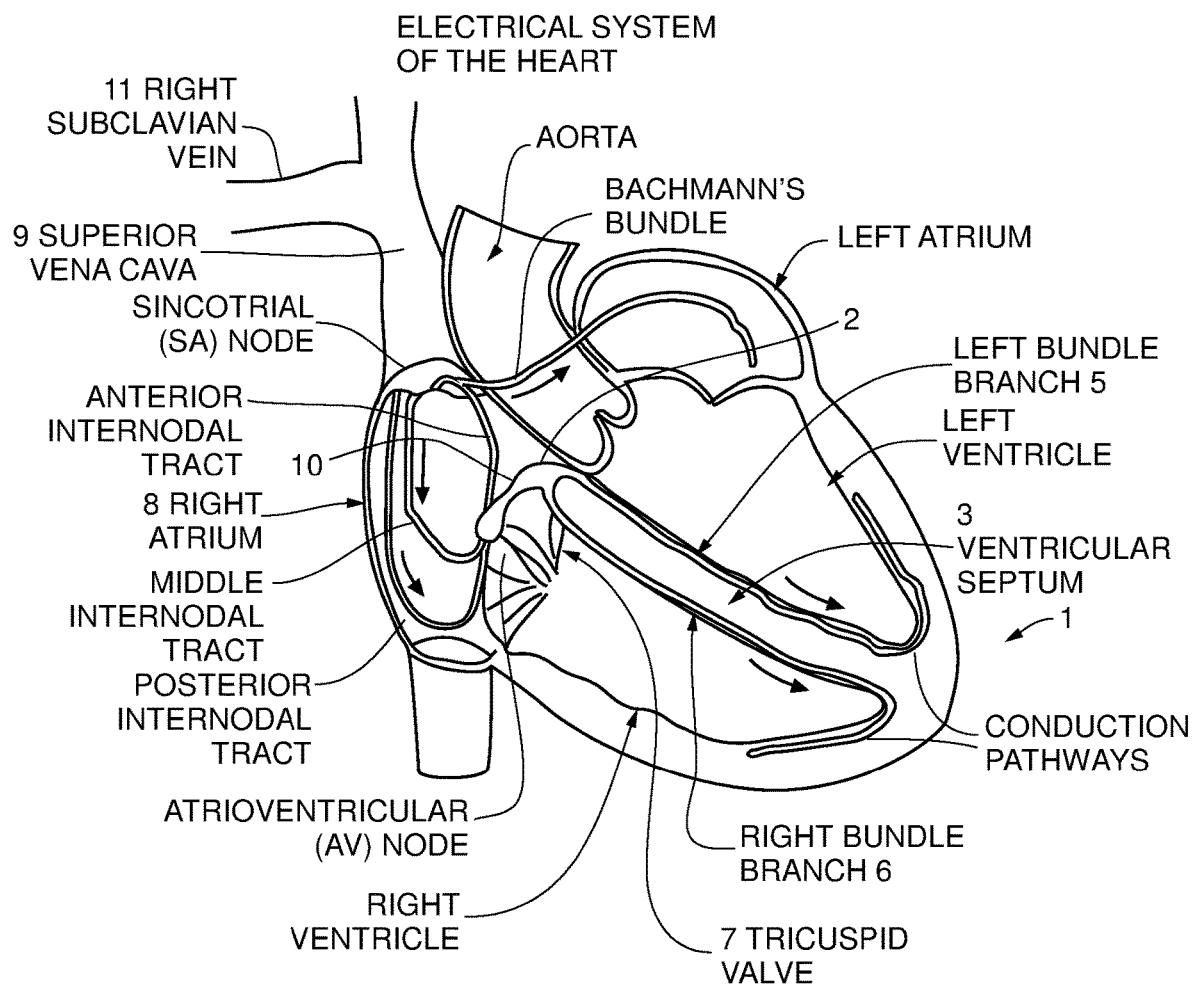
FIG. 1 is a cross-sectional illustration of a human heart depicting the anatomy of the heart and its electrical system.

For contextual understanding, of how embodiments of the disclosure are intended to function, FIG. 1 is included to illustrate the structure of a typical human heart 1 with relevant anatomical features shown. As mentioned, one embodiment of the disclosure is directed to a method for deploying an electrical lead to the His bundle 2 at a target site 10 along the septum 3 distal to the atrioventricular (AV) node 4, but proximal to the left branch bundle (LBB) 5 and the right branch bundle (RBB) 6. Such a target site 10 for proper deployment of a pacing lead, is depicted in FIG. 1 at the crest of the ventricular septum 3 on the atrial aspect of the annulus of the tricuspid valve septal leaflet 7 within the right atrium 8. The remaining FIGS. 2-7 depict embodiments of a catheter suitable for accessing the heart and reaching the target site 10 and the manner in which such a catheter is used.

An example of a catheter 20 suitable for use in reaching the target site 10 from the subclavian vein is illustrated in FIGS. 2-7.

Figure 2:
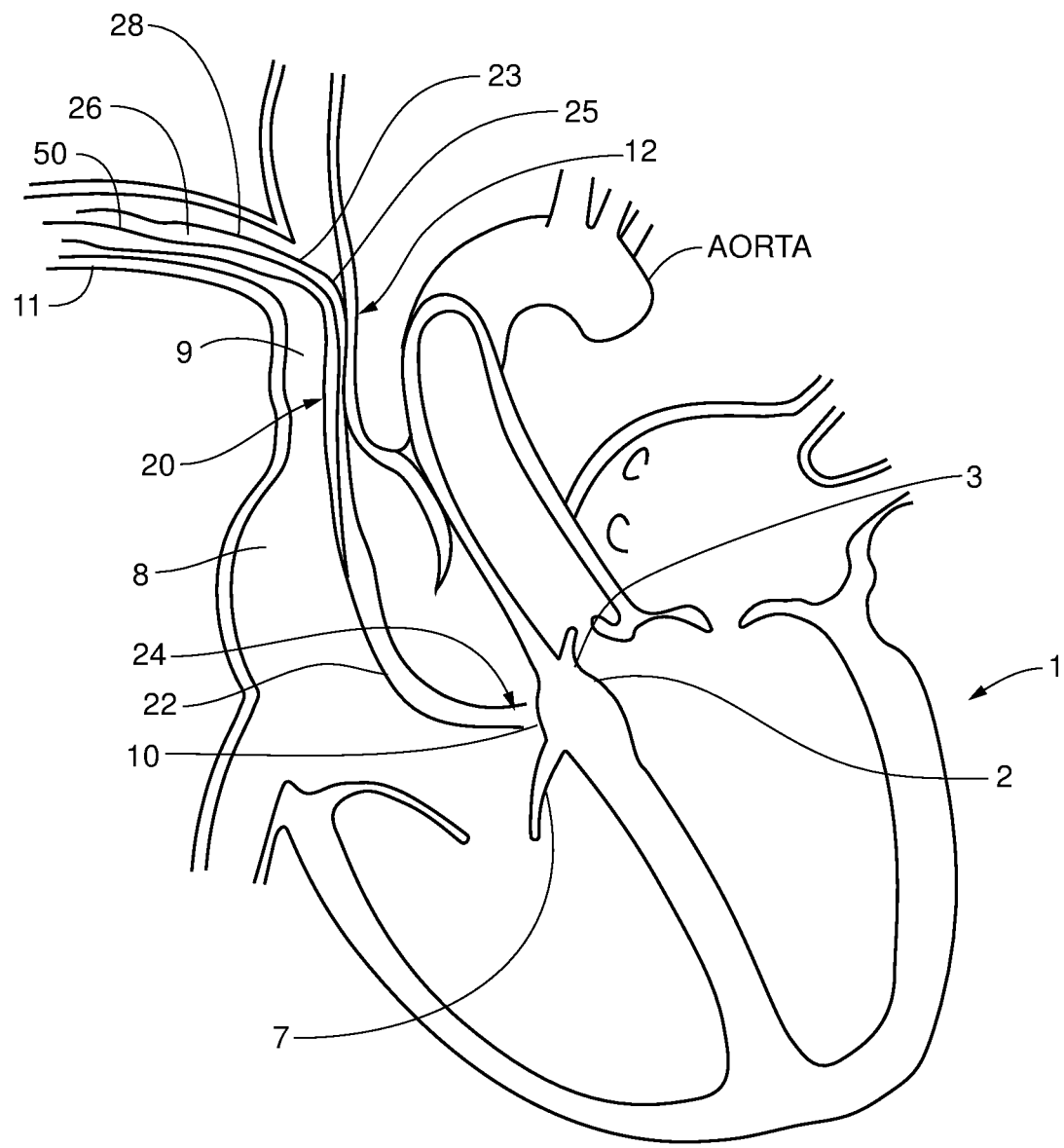
FIG. 2 is a cross-sectional illustration of a human heart wherein an embodiment of a guide catheter is shown advanced to a target site within the central fibrous body, between the tricuspid valve and the aortic valve and corresponding to the bundle of his.

FIG. 2 is the schematic diagram of FIG. 1 in which a distal portion or end region 22 of delivery catheter 20 is shown extending into the right atrium 8 of the heart 1, from the superior vena cava 9 and the right subclavian vein 11, with the distal tip 24 positioned at the target site 10.

According to one method, an operator/physician positions guide wire 50 into the heart 1, for example via a "sub-clavian stick" or central venous access procedure such as is illustrated in FIG. 3. Accordingly, the catheter 20 is passed over the guide wire and—advanced into the superior vena cava 9 from the right subclavian vein 11 and into the right atrium 8 such as is in the manner shown in FIG. 2. A wall 12 of the superior vena cava 9 provides back-up support for distal portion 22 as the operator maneuvers tip 24 into a proper substantially perpendicular orientation with the septum 3 at the target site 10, such as in the manner shown in FIG. 4.

In FIG. 4, a close up view of the distal tip 24 is shown following advancement of medical electrical lead 30 though a lumen 26 of the catheter 20 to the target site 10. The lead 30 is extended distally from distal tip 24 and implanted into the septum 3 by clockwise rotation of the lead body to provide pacing to the heart 1 via the bundle of his 2.

As is shown in FIG. 2, the wall 12 of the superior vena cava 9 acts to provide a stabilizing surface or brace for distal portion 22 so as to direct and force the shaft 28 of the catheter 20 into the right atrium 8 from the subclavian vein 11. Wall 12 forces a specialized zone of the catheter 20 to bend with the shape of the superior vena cava 9. Because the default or at rest shape of the catheter 20 included a unique shape for aligning the distal tip 24 with the target site 10 (discussed in greater detail below), a guidewire 50 may be advanced through the lumen 26 to aid in tracking the catheter 20 through the confines of the vessel anatomy. Once the distal region 22 of the catheter 20 is within the right atrium 8 the guidewire 50 is removed.

The bracing affect provided by the vessel wall 12 imbues the proximal region 23 of the catheter 20 with a proximal bend 25. This bend 25 cooperates with the unique shape of the distal region 22 such that once the catheter 20 is advanced from the subclavian vein 11, and through the superior vena cava 9 and into the right atrium 8 the catheter tip 24 is automatically positioned to be perpendicularly oriented with the septum 3 wall in the area of the target site 10 such as in the manner shown in FIG. 4.

As indicated, the shape if the catheter 20 is unique. The catheter 20, such as is shown in FIGS. 5-7 is an elongate shaft 28, which defines a central lumen 26 extending along its length, and having a substantially straight proximal region ("straight" meaning without bend, or having a curve of essentially infinite radius) 23 and a curved distal region 22. The distal region 22 is of specialized shape and construction wherein a specific shape and curve is provided to the distal region 22. As described above, this pre-formed shape cooperates with surrounding venous and heart anatomy, to ensure proper orientation and positioning of the distal tip 24 at the target site 10 when the catheter 20 is advanced into the right atrium 8 such as by the right side access procedure shown in FIGS. 2 and 3. It should also be noted that in some embodiments, the catheter 20 such as is shown in FIGS. 5-7 may also be suitable for use in a left side access electrode implantation procedure such as is described in U.S. Pat. No. 8,606,369, issued on Dec. 10, 2013, the entire contents of which is incorporated herein by reference.

The particular shape of the distal region 22, is illustrated in FIG. 5 wherein it may be seen that the catheter 20 in an "at rest" state (prior to use) has a substantially straight proximal region 23 and a distal region 22 forming a semicircular hook or J-shape. The shape of the distal region 22 defines a centerline radius a of approximately 180 degrees with a radius (indicated by line 40) of approximately 0.3-0.6 inches, as measured from the axis 44 of the catheter 20. In at least one embodiment the radius 40 is 0.4 inches. In at least one embodiment radius 40 is 0.5 inches.

In addition, and as is shown in FIG. 6, the distal tip 24 forms the half turn of a left-hand helix having a pitch 47 of zero inches to about 0.4 inches as measured from the distal tip 24 to the plane 46 defined by the surface of the proximal region 23 in the at rest state and adjacent to the distal region 22. In at least one embodiment the pitch 46 is 0.3 inches.

In an alternative embodiment to that in FIGS. 5-6, catheter 20 is provided with a proximal bend 25 when in the pre-insertion or default formed state. The embodiment shown in FIG. 8 is distinct from that shown in FIG. 5, as the embodiment shown in FIG. 5 requires the anatomy of the superior vena cava 9 and associated anatomy to imbue the proximal region 23 of the catheter 20 with the bend 25, whereas in the embodiment shown in FIG. 8 the proximal region 23 of the catheter 25 is formed with a bend 25, and which is apparent even in the pre-insertion state shown.

The particular characteristic of the bend 25, is that it has a radius 48 of approximately 2.0 inches to 4.0 inches, along a length 49 of the proximal region 23 of approximately 2.0 inches to 4.0 inches as well. In at least one embodiment, the radius 48 is approximately 3.0 inches and the length 49 is also approximately 3.0 inches. The bend 25 begins at a point approximately 3.0 inches to 4.0 inches distally from the distal region 22; that is to say, a substantially straight portion 45 of the proximal region 23 extends 3.0 to 4.0 inches between the distal end of the bend 25 and the distal region 22 of the catheter 20. In at least one embodiment the length of the substantially straight portion 45 is approximately 3.5 inches.

Figure 8:
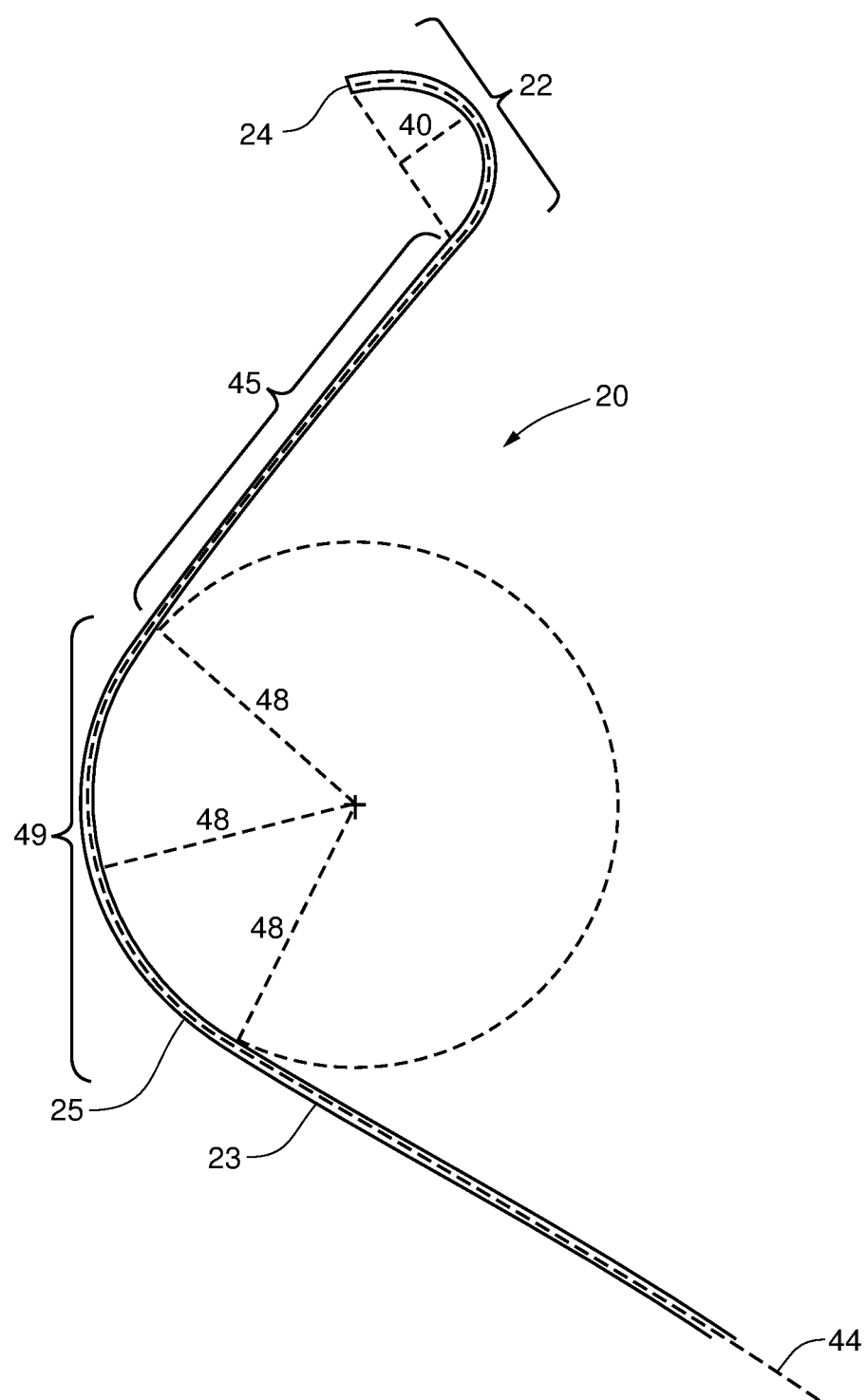
FIG. 8 is a side perspective view of an alternative embodiment of the catheter shown in FIG. 5 having a pre-formed bend in the proximal region of the catheter shaft.

In the embodiment shown in FIG. 8 the pitch 47 of the distal tip 24, may be the same as that in other embodiments and range from zero to about 0.4 inches; and in at least one embodiment is 0.3 inches. The depiction of this pitch 47 is identical to that shown in the embodiment of FIGS. 5-6.

In the embodiment shown in FIG. 8 the bend 25 provides a shape that encourages the catheter 20 to advance through and around the anatomy of the right subclavian vein and superior vena cava with less resistance and ease of advancement in some anatomies. The preformed bend 25 also encourages perpendicular alignment of the distal tip 24 with the target site 10 as described above (and below) and shown in FIG. 4.

For purposes of describing the shape of the catheter 20, here the terms "approximately" and "substantially" are used to take into account minor machine and formation tolerances. When the values mentioned above are measured with normal instruments readily available to one of ordinary skill in the art such as a protractor or ruler the describe values will be accurate.

The particular combination of the curvature of the distal region 22 and the out of plane angle of the distal tip 24 enables the catheter 20 to form a perpendicular angle γ with the septum 3 such as in the manner shown in FIG. 4. The ability of the catheter 20 to form a perpendicular angle relative to the septum 3 provides an idealized approach angle for the implantation of the electrical lead 30, which makes it easier for the helical screw of the lead 30 to bite into the tough endocardial membrane of the septum 3 and more easily seat therein. Once the lead 30 is properly implanted into the septum 3 at the target site 10, the catheter is removed.

By more accurately positioning the lead 30 at the target site 10, and more readily penetrating into the septum 3, the catheter 20 provides for a safer procedure and a total implant procedure time and fluoroscopy time that is feasible and acceptable to pacemaker implanters. In addition, by positioning the lead 30 in the manner described the lead is more effectively seated within septum to more efficiently pace the bundle of his. Published studies find a mean pacing capture thresholds that is one volt lower than the mean threshold of 2.5 volts that is reported using prior catheters, those not capable of perpendicular electrode placement.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A method comprising:
    inserting a catheter into a right subclavian vein of a patient, the catheter comprising:
        an elongate catheter shaft having a proximal region and a distal region along a length of the catheter, the catheter shaft defining a lumen extending along the length of the catheter, the catheter shaft having a default shape wherein the distal region forms a hook including a curve,
        wherein the distal region terminates at a distal tip of the catheter shaft;
    advancing the catheter along the right subclavian vein and into a superior vena cava and finally into a right atrium of a heart of the patient such that, with the proximal region braced by a wall of the superior vena cava, the distal region returns to the default shape, the default shape of the distal region causing the distal tip of the catheter to align itself against a septal wall of the right atrium corresponding to a target site; and
    threading a guidewire through the lumen of the catheter shaft,
    wherein inserting the catheter into the right subclavian vein of the patient includes inserting the guidewire and the catheter into the right subclavian vein.

2. The method of claim 1, further comprising:
    advancing a pacing lead through the lumen of the catheter to the target site; and
    implanting the pacing lead through the septal wall and into a septum at the target site.

3. The method of claim 2, further comprising removing the catheter from the patient following implantation of the pacing lead.

4. The method of claim 1, wherein the proximal region is substantially straight in the default shape.

5. The method of claim 1,
    wherein the curve of the distal region has a radius of 0.3 inches to 0.6 inches, and
    wherein the curve of the distal region has a pitch between 0.1 and 0.4 inches.

6. The method of claim 5,
    wherein the radius is approximately 0.35 inches to 0.45 inches, and
    wherein the pitch is approximately 0.25 inches to 0.35 inches.

7. The method of claim 1, wherein the curve of the distal region defines an arc of approximately 180 degrees.

8. The method of claim 1, wherein an outer diameter of the catheter shaft is between 6 French and 14 French.

9. The method of claim 1, wherein an outer diameter of the catheter shaft is between 6 French and 7.5 French.

10. The method of claim 1, wherein the curve of the distal region includes a left-hand helix.

11. The method of claim 1, wherein the default shape of the distal region causes the distal tip of the catheter to align itself in a substantially perpendicular orientation against the septal wall of the right atrium corresponding to the target site.

12. The method of claim 1, wherein the target site is a region of the septal wall corresponding to and containing a bundle of HIS.

13. The method of claim 1, further comprising:
    advancing a pacing lead through the lumen of the elongate catheter shaft;
    and
    implanting the pacing lead, via the distal tip, through a region of the septal wall corresponding to and containing a bundle of HIS.

14. A method comprising:
    inserting a catheter into a right subclavian vein of a patient, the catheter comprising:
        an elongate catheter shaft having a proximal region and a distal region along a length of the catheter, the catheter shaft defining a lumen extending along the length of the catheter, the catheter shaft having a default shape wherein the distal region forms a hook including a curve,
        wherein the distal region terminates at a distal tip of the catheter shaft; and
    advancing the catheter along the right subclavian vein and into a superior vena cava and finally into a right atrium of a heart of the patient such that, with the proximal region braced by a wall of the superior vena cava, the distal region returns to the default shape, the default shape of the distal region causing the distal tip of the catheter to align itself against a septal wall of the right atrium corresponding to a target site,
    wherein the proximal region includes a bend in the default shape, the bend in the default shape turning in an opposing direction relative to the curve of the distal region, and
    wherein the proximal region further includes a substantially straight portion having a length of approximately 2.0 inches to 4.0 inches, and extending from a distal end of the bend to a proximal end of the curve of the distal region.

15. The method of claim 14, wherein the bend of the proximal region encourages perpendicular alignment of the distal tip with the target site.

16. The method of claim 14, wherein the bend of the proximal region is defined by a portion of the catheter shaft having a radius of approximately 2.0 inches to 4.0 inches and a length of approximately 2.0 inches to 4.0 inches.

17. The method of claim 16, wherein the substantially straight portion has a length of approximately 3.0 inches to 4.0 inches.

18. The method of claim 17,
    wherein the radius of the portion of the catheter shaft defining the bend is approximately 2.5 inches to 3.5 inches, and
    wherein the length of the bend is approximately 2.5 inches to 3.5 inches.

19. A method comprising:
    inserting a catheter into a right subclavian vein of a patient, the catheter comprising:
        an elongate catheter shaft having a proximal region and a distal region along a length of the catheter, the catheter shaft defining a lumen extending along the length of the catheter, the catheter shaft having a default shape wherein the distal region forms a hook including a curve, wherein the distal region terminates at a distal tip of the catheter shaft; and advancing the catheter along the right subclavian vein and into a superior vena cava and finally into a right atrium of a heart of the patient such that, with the proximal region braced by a wall of the superior vena cava, the distal region returns to the default shape, the default shape of the distal region causing the distal tip of the catheter to align itself against a septal wall of the right atrium corresponding to a target site, wherein the proximal region is substantially straight in the default shape, and wherein a bracing affect provided by the wall of the superior vena cava imbues the proximal region with a bend.

20. The method of claim 19, wherein the bend of the proximal region cooperates with the curve of the distal region to perpendicularly orient the distal tip with the septal wall.

21. The method of claim 19, further comprising:

advancing a pacing lead through the lumen of the elongate catheter shaft; and implanting the pacing lead, via the distal tip, through a region of the septal wall corresponding to and containing a bundle of HIS.

* * * * *